(12) United States Patent
Osajima et al.

(10) Patent No.: US 7,112,571 B2
(45) Date of Patent: Sep. 26, 2006

(54) PEPTIDE Y-2

(75) Inventors: Katsuhiro Osajima, Yawatahama (JP); Eiji Seki, Ohzu (JP); Mayumi Yoshida, Ohzu (JP)

(73) Assignee: Senmi Ekisu Co., Ltd., Ehime-ken (JP)

( * ) Notice: Subject to any disclaimer, the term of this patent is extended or adjusted under 35 U.S.C. 154(b) by 459 days.

(21) Appl. No.: 10/266,609

(22) Filed: Oct. 9, 2002

(65) Prior Publication Data

US 2003/0148923 A1 Aug. 7, 2003

Related U.S. Application Data

(62) Division of application No. 09/720,481, filed as application No. PCT/JP99/04287 on Aug. 9, 1999, now abandoned.

(30) Foreign Application Priority Data

Apr. 28, 1999 (JP) ................. 11-122404

(51) Int. Cl.
*A61K 38/05* (2006.01)
(52) U.S. Cl. ............... 514/19; 514/2; 514/21; 424/439; 426/657
(58) Field of Classification Search .......... 514/2, 514/19, 21; 424/439; 426/657
See application file for complete search history.

(56) References Cited

U.S. PATENT DOCUMENTS

| | | |
|---|---|---|
| 4,853,231 A | 8/1989 | Osajima et al. |
| 4,981,699 A | 1/1991 | Inada et al. |

FOREIGN PATENT DOCUMENTS

JP 5-271297 * 10/1993

OTHER PUBLICATIONS

English Abstract of JP-6-249000 (Sep. 6, 1994).*
English Abstract opf JP-6-239897 (Aug. 30, 1994).*
English Abstract of JP-11-228599 (Aug. 24, 1999).*
English Abstract of JP-11-80018 (Mar. 23, 1999).*
H. Cheung et al., *J. Biol. Chem.*, vol. 255, No. 2, pp. 401-407 (Jan. 25, 1980).
Abstract of The Congress of Japan Society for Bioscience, Biotechnology and Agrochemistry, vol. 67, No. 3, 1993 (English Translation).
T. Kawasaki et al., "Hypotensive Effect of a Short Chain Peptide, Valyl-tyrosine, Derived from Sardine Protein on Subjects with Slight Hypertension",The 21st Annual Scientific Meeting of the Japanese Society of Hypertension, Sep. 24-26, 1998.
T. Kawasaki et al., Journal of Hypertension, Abstracts presented at the 17th Scientific Meeting of the International Society of Hypertension, Jun. 7-11, 1998, Amsterdam, Netherlands, Abstract Nos. 3XP2, 11Z.3, P17.43.
T. Matsui et al., *Biosci. Biotech. Biochem.*, 57 (6) 922-925, 1993.

* cited by examiner

*Primary Examiner*—David Lukton
(74) *Attorney, Agent, or Firm*—Birch, Stewart, Kolasch & Birch, LLP (57) ABSTRACT

Peptide which is obtained by treating fish meat such as sardine with an alkaline protease is adsorbed with a peptide-adsorbing resin (such as ODS resin) and eluted with 10 aqueous ethanol to obtain a peptide (Y-2 fraction). The resulting novel peptide has an excellent hypotensive action and can be used as a nutrient and a specific health food and, in addition, it can be advantageously used as a hypotensive agent.

8 Claims, 9 Drawing Sheets

PEPTIDE Y-2

This application is a divisional of application Ser. No. 09/720,481, filed May 23, 2001, now abandoned, which is a 371 of PCT/JP99/04287 filed Aug. 9, 1999, which claims priority to Japanese application 11-122404 filed Apr. 28, 1999.

TECHNICAL FIELD OF THE INVENTION

The present invention relates to a novel peptide and also to a method for manufacturing the same and further to its hypotensive use.

PRIOR ART

The present inventor et al. previously obtained a peptide α-1000 which has an ACE-inhibiting activity, through a process comprising thermally denaturing fish meat, then hydrolyzing it with a neutral or alkaline protease, inactivating the enzyme used, and finally separating the peptide (JP-A-5-271297).

PROBLEMS TO BE SOLVED BY THE INVENTION

The present invention is that, in order to develop a substance which is not only excellent in a hypotensive action but also is highly safe, investigations have been done from various viewpoints in consideration of importance of hypotension and an object of the present invention is to isolate a novel peptide having a strong ACE (angiotensin conversion enzyme) inhibiting activity from peptide α-1000 which was previously developed by the present inventor et al.

MEANS FOR SOLVING THE PROBLEMS

In order to achieve the above-mentioned object, the present inventor et al have carried out an intensive study where an aqueous solution of peptide α-1000 is treated with a peptide-adsorbing resin (ODS resin) and eluted with a 10% ethanol to give a Y-2 fraction and have not only confirmed that the Y-2 fraction is a novel peptide but also, to be noteworthy, that actually confirmed of its effect by carrying out a human in vivo hypotensive test using human being as actual objects to be tested (that was already approved by the Human Investigation Review Committee of the Institute of Health Science, Kyushu University") whereby the present inventor et al have succeeded in accomplishing the present invention.

Thus, the present invention relates to a hypotensive system using Y-2, a novel peptide, as an effective ingredient and the very big characteristic feature of the present invention is that Y-2 is not only a novel substance which has not been known yet but also has been confirmed to have an excellent hypotensive action, further that the hypotensive action is not confirmed by the conventional method of measuring the ACE-inhibiting activity or, in other words, by an indirect method but by measurement of the blood pressure directly or, in other words, by a direct method and furthermore that confirmation of the hypotensive action is not carried out by the conventional method using animals such as rats and mice but by a method of measuring the human blood pressure directly.

Thus, the present invention is very characteristic and quite epoch-making in such a respect that a hypotensive action or, in fact, a quite excellent hypotensive action has been successfully confirmed by a direct method (clinical test) where Y-2 is directly administered to human being to directly measure the blood pressure of the human being instead of by animal test or by an indirect method where degree of inhibition of enzymes is measured and further that its safety and easiness in administration and in manufacture of pharmaceutical preparations and food/beverage products have been confirmed for human beings.

Now, the invention will be described in detail as hereunder. First mentioned is peptide α-1000 which is used as a source material of peptide Y-2 of the invention.

Peptide α-1000 is separated from fishes and shellfishes and, for example, it may be prepared according to JP-A-5-271297. First, fishes and shellfishes are processed in meat collectors, deboners or the like to separate their meat. It is desirable that the raw materials are as fresh as possible. The separated meat is ground and divided into plural lumps of ground fish meat weighing about 10 kg each, and these meat lumps could be subjected to the next treatment but, if desired, they may be rapidly frozen with a spray of cold air of a temperature falling between −50 and −20° C., for example, at about −30° C., and stored at a temperature falling between −25 and −20° C. whereby, if necessary, that may be used appropriately.

The fishes and shellfishes usable herein include, for example, fishes with red flesh, such as sardine, saurel, tuna, bonito, saury, mackerel, etc.; fishes with white flesh, such as flounder, sea bream, sillaginoid, gizzard shad, cod, herring, yellowtails, etc.; cartilaginous fishes such as shark, ray, etc.; freshwater fishes such as pond smelt, carp, char, "yamame" (a kind of trout), etc.: deep-sea fishes such as granulose, anglerfish, etc.; as well as lobster, prawn, shrimp, crab, octopus, opossum shrimp, etc.

The fish and shellfish meat collected is ground with a meat grinder or the like, to which is added water of from ½ to 20 times, but preferably from 1 to 10 times by weight the meat. Then, this is heated thereby to inactivate the autolytic enzyme existing therein and also to kill the bacteria, simultaneously with the protein constituting it being thereby thermally denatured so as to increase the subsequent enzymatic reaction efficiency. For heating it, employable is any condition capable of producing the intended results and, for example, it may be heated in the temperature range of not lower than 65° C. for a period of from 2 to 60 minutes or preferably not lower than 80° C. for a period of from 5 to 30 minutes.

Next, an alkaline agent such as aqueous ammonia or an aqueous solution of sodium (or potassium) hydroxide or the like is added thereto so as to make the meat have a pH value suitable to a protease with which the meat is to be processed.

(For example, for alkaline proteases, the pH of the meat may be at least 7.5, but preferably at least 8.) The meat is then heated at a temperature also suitable to the protease (for example, at a temperature falling between 20 and 65° C., though depending on the type of the protease to be used; for example, for alkaline proteases, the meat is heated at a temperature falling between 35 and 60° C. or, preferably, between 40 and 55° C.) and the meat is processed with a protease for a period of from 30 minutes to 30 hours (for example, in the case of an alkaline protease, for a period of from 30 minutes to 25 hours or, preferably, from 1 to 17 hours).

Any and every protease capable of degrading protein in neutral or alkaline conditions is employable herein and one or more proteases may be used either singly or as combined. For their origins, proteases for use herein may be derived not only from animals and vegetables but also from microorganisms and they cover a broad range of various proteases, including, for example, pepsin, renin, trypsin, chymotrypsin, papain, bromelain, as well as bacterial proteases, filamentous proteases, actinomycelial proteases, etc. Usually, these enzymes which are available in the market may be used but, depending on their applications and upon necessity, also usable are non-purified enzymes as well as solid or liquid, enzyme-containing substances, such as enzyme-containing cultures and koji (malted rice or malt). The amount of the enzyme to be added may fall between 0.1% and 5.0% or so.

If desired, the thus-processed meat is then neutralized, and heated at the temperature of not lower than 70° C. (or, preferably, not lower than 80° C.) for a period of from 2 to 60 minutes (or, preferably, from 5 to 30 minutes) so as to inactivate the enzyme used and to facilitate the separation of the intended peptide from it. The meat having been subjected to heat treatment for enzyme inactivation as such is then passed through a vibro-screen or the like to remove coarse impurities from it, thereafter optionally passed through Jector, and finally subjected to ultra-centrifugation to remove the floating impurities and the precipitated impurities from it.

Next, the obtained product is filtered using a filter aid such as diatomaceous earth or the like (e.g., Celite), and the obtained filtrate is processed with activated carbon so as to deodorize, decolor and purify it (for which the amount of activated carbon to be used may be from 0.05 to 20 w/v % or, preferably, from 0.1 to 10 w/v % and the treatment with activated carbon may be effected at a temperature falling between 20 and 65° C., but preferably between 25 and 60° C., for a period of from 15 minutes to 4 hours, but preferably from 30 minutes to 2 hours).

The purified product is then concentrated in any ordinary manner, for example, under reduced pressure (at a temperature falling between 0 and 50° C. to a degree of 30 Bx or so). If desired, this is again subjected to (ultra)centrifugation or filtration to obtain a peptide solution. The thus-obtained peptide solution is sterilized (through UHTST or in any other ordinary manner), and filled into containers to give a product (α-1000 (liquid)). If desired, this may be further concentrated or may be even diluted, or may be powdered in any ordinary manner of spray-drying, freeze-drying or the like into a powdery product of 60-mesh or so and the powder may be packed in bags or any other containers to give a product (α-1000 (powder)). These products are stored in refrigerators or freezers.

The liquid, pasty or powdery peptide obtained as such is α-1000.

The physicochemical properties of peptide α-1000 (in the form of spray-dried powder) are shown in the following Table 1, Table 2 and Table 3.

TABLE 1

Physicochemical Properties of Peptide α-1000 (powder) (1)

(A) Molecular weight:
200 to 10,000 (measured by Sephadex G-25 column chromatography).
(B) Melting point:
Colored at 119° C. (decomposition point).
(C) Specific rotatory power:
$[\alpha]_D^{20} = -22°$.
(D) Solubility in solvents:
Easily soluble in water; but almost insoluble in ethanol, acetone and hexane.
(E) Chemical differentiation in acidic, neutral or basic character:
Neutral, pH of from 5.0 to 8.0 (10% solution).
(F) Appearance, and constituent components:
White powder, comprising 5.14% of water (in reduced-pressure, heat drying method), 87.5% of protein (in Kjeldahl method with a nitrogen/protein conversion coefficient of 6.25), 0% of lipid (in Soxhlet extraction method), and 5.0% of ash (in direct ashing method).

TABLE 2

Physicochemical Properties of Peptide α-1000 (powder) (2)

Figure 1:
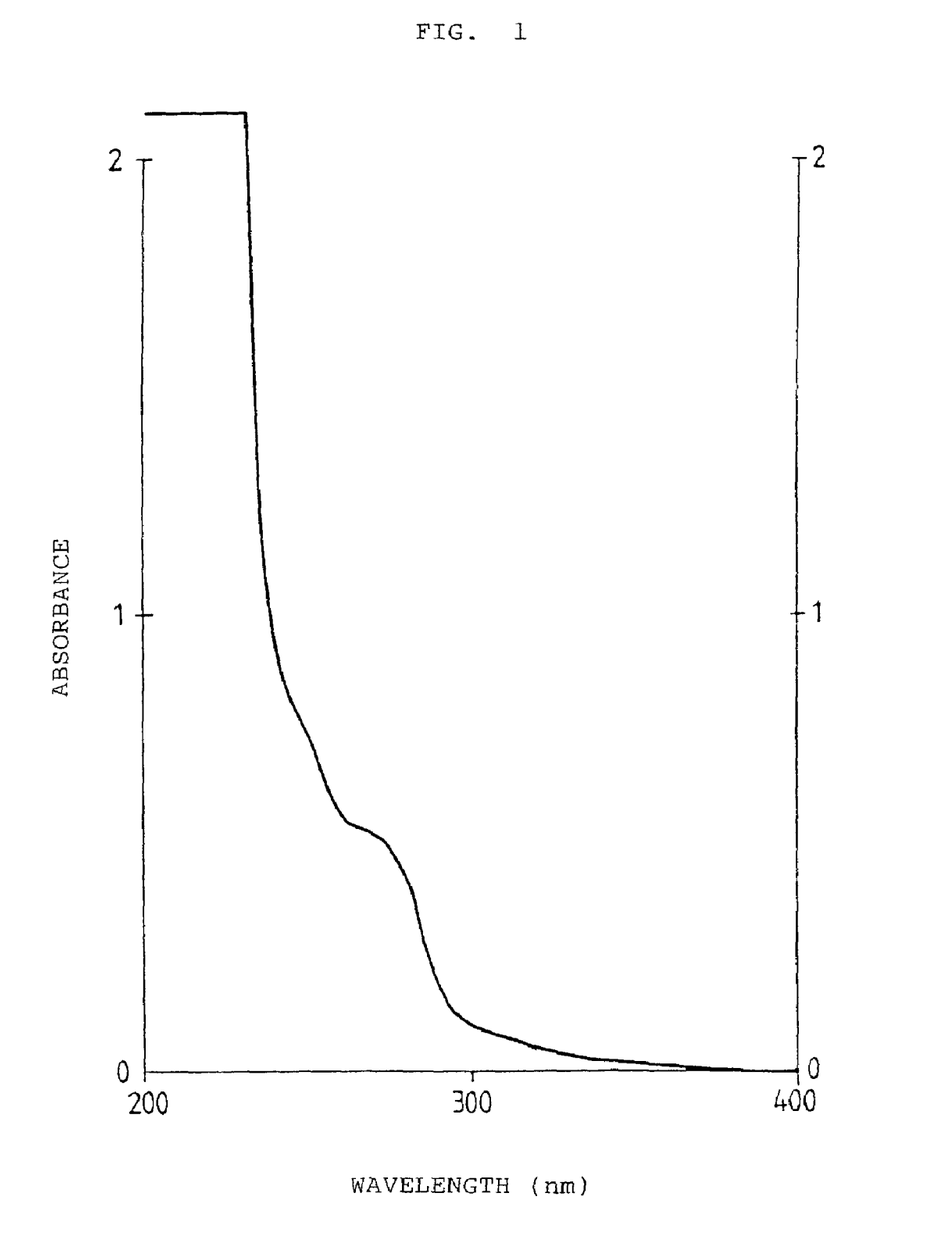
FIG. 1 is a pattern of the UV spectrum of peptide α-1000.
Figure 2:
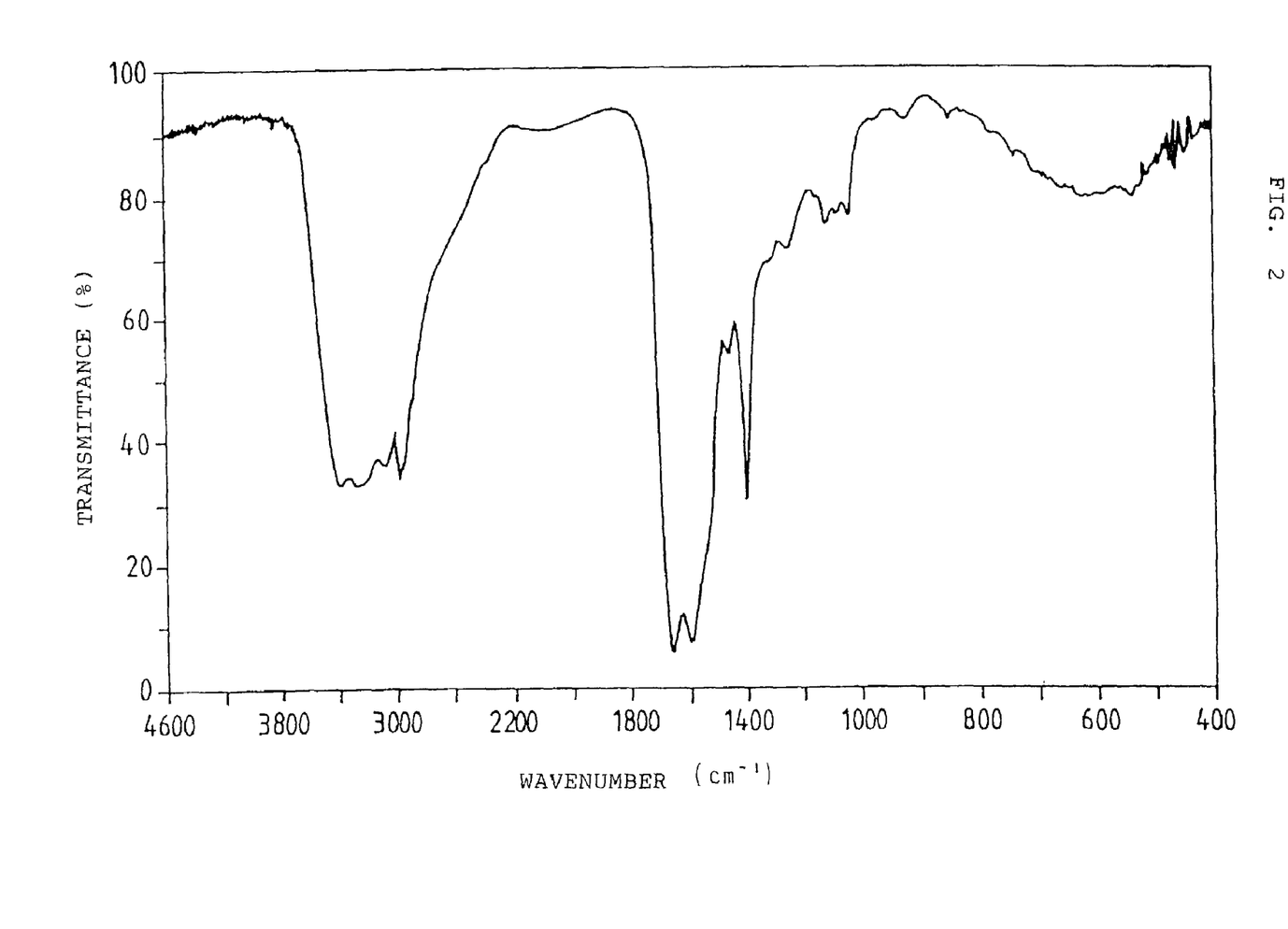
FIG. 2 is a pattern of the IR spectrum of peptide α-1000.

(G) UV spectrum:
As shown in FIG. 1.
(H) IR spectrum:
As shown in FIG. 2.
(I) Characteristics:
Peptide derived from fish meat and obtained by inactivating an autolytic enzyme by heating followed by hydrolyzing with protease.
(J) Amino acid composition:
As shown in Table 3.

TABLE 3

Amino Acid Composition of Peptide α-1000 (Powder)

| Items for Analytical Test | Result (%) | Analytical Method |
|---|---|---|
| Total Amino Acid | | Automatic Analysis |
| Arginine | 3.34 | of Amino Acids |
| Lysine | 6.86 | (except that |
| Histidine | 3.34 | cystine was |
| Phenylalanine | 2.33 | oxidized with |
| Tyrosine | 2.01 | formic peracid |
| Leucine | 6.35 | followed by |
| Isoleucine | 3.27 | hydrolyzing with |
| Methionine | 2.26 | hydrochloric acid |
| Valine | 4.16 | and that tryptophan |
| Alanine | 5.17 | was analyzed by |
| Glycine | 3.59 | means of high |
| Proline | 2.15 | performance liquid |
| Glutamic acid | 12.35 | chromatography) |
| Serine | 3.30 | |
| Threonine | 3.70 | |
| Aspartic acid | 8.36 | |
| Tryptophan | 0.32 | |
| Cystine | 0.47 | |
| Total Amount | 73.33 | |

Directly when liquid, but after water is added thereto when powdery, peptide α-1000 thus prepared in the manner noted above is passed through a peptide-adsorbing resin such as ODS resin or the like, then washed with water or the like, and thereafter eluted in order with varying concentrations of ethanol or the like to give each of the fractions. Among those, fractions having strong hypotensive activity were fractionated and subjected to necessary treatments such as concentration and drying to give a hypotensive component. For example, a fraction Y-2 obtained by eluting with 10% ethanol showed an excellent hypotensive activity.

The peptide Y-2 in accordance with the present invention is a novel substance which has not been known yet, shows an excellent hypotensive activity and has no problem for its safety and, accordingly, it can be used as a hypotensive agent and also as a peptide for foods for specified health uses with an object of hypotension. Therefore, the present peptide can be used as additives for foods such as condiments and nutrient supplements and animal feeds and, in addition, it can be widely used, due to the above-mentioned specific physiological activity, as pharmaceuticals for prevention or, in some cases, for therapy of hypertensive diseases and also as infusions, health foods, nutrient supplements for clinical use, etc.

When it is used as foods, it may be appropriately used according to conventional methods such as that the peptide is added as it is or is used together with other foods or food components. When it is used as pharmaceuticals, it may be administered either orally or parenterally. In the case of oral administration, it may be made into tablets, granules, powder preparations, capsules, diluted powder preparations, drinks, etc. by a conventional methods for example. In the case of parenteral administration, it may be used as injection preparations, drips, suppositories, etc. for example.

The present invention will now be illustrated in more detail by way of the following Referential Example and Examples.

REFERENTIAL EXAMPLE

Fresh sardines were processed in a deboner to collect the meat. The meat was ground and divided into plural lumps of ground fish meat weighing 10 kg each, and these meat lumps were rapidly frozen at a temperature not higher than −30° C. Then, each meat lump was milled in a mill, to which was added water of the same amount as that of the meat. The resulting mixture was fed into a tank, then heated therein at 100° C. for 10 minutes, whereby the autolytic enzyme in the meat was inactivated and the meat was thermally denatured. Next, aqueous ammonia was added to this, with which the pH value of the processed meat was adjusted to be 9.5.

0.1% solution of a commercially-available alkaline protease was added thereto. Then, the resulting meat was kept heated at 50° C. for 17.5 hours so as to be decomposed with the enzyme added thereto. Next, this was boiled for 15 hours to inactivate the enzyme used.

This was then passed through a vibro-screen (150 meshes) and then treated by Jector (at 5000 rpm), and thereafter processed in a sharpless centrifugal separator (at 15000 rpm). Then, this was filtered using diatomaceous earth as a filter aid and the resulting filtrate is used as a peptide liquid.

Activated carbon was added to the obtained peptide liquid in an amount of 1 w/v %, then stirred at 30° C. for 60 minutes, and thereafter filtered. The filtrate was concentrated under reduced pressure (at 20° C.) in an ordinary manner, and then sterilized through UHTST also in an ordinary manner to obtain an α-1000 product (liquid). This was further spray-dried in an ordinary manner into an α-1000 product (powdery) having a particle size of 60 meshes. Each of these products was frozen and stored.

The peptide α-1000 (powdery) prepared as such was filtered through a gel of Sephadex G-25 in a column under the condition mentioned below, and its molecular weight was found to be from 200 to 10,000.

Column size: 16 ϕ×950 mm.

Eluent: 0.1 M phosphate buffer (pH 7.0).

Fractionation: 2 ml/tube.

Flow rate: 10 ml/hr.

Molecular weight marker: bacitracin (molecular weight: 1450).

The peptide α-1000 (liquid) obtained as above had a water content of 73.6% (as measured in a reduced-pressure heat drying method), and was pale yellow. Its 10% solution had pH of 7.5. This gave no fish smell and was not bitter. Analysis of the components and measurement of the amino acid composition thereof were carried out and the results shown in the following Table 4 and Table 5 were obtained.

TABLE 4

Analysis of Components of Peptide α-1000 (Liquid)

| Items for Analytical Test | Result | Analytical Method |
|---|---|---|
| Protein | 24.8% | Kjeldahl method (*1) |
| Lipid | 0% | Soxhlet extraction |
| Ash | 1.6% | Direct ashing method |
| Fiber | 0% | Modified Henneberg-Stohman method |
| Saccharide | 0% | (*2) |
| Energy | 99 kcal/100 g | (*3) |
| Amino-type Nitrogen | 1.2% | Van Slyke method |
| Iron | 0.11 mg/100 g | o-Phenanthroline absorptiometry |
| Calcium | 4.5 mg/100 g | Atomic absorption spectrometry |
| Sodium | 211 mg/100 g | Atomic absorption spectrometry |
| Heavy Metals (as Pb) | 1.9 ppm | Sodium sulfide colorimetry |
| Arsenic (as $As_2O_3$) | 3.7 ppm | DDIC-Ag absorption spectrometry |
| Histamine | not detected | HPLC |

Notes:
(*1) Nitrogen protein conversion coefficient: 6.25
(*2) Calculating formula: 100 − (water content + protein + lipid + fiber + ash)
(*3) Energy conversion coefficient: protein, 4; lipid, 9; carbohydrate (fiber + saccharide), 4

TABLE 5

Amino Acid Composition of Peptide α-1000 (Liquid)

| Items for Analytical Test | Result (%) | Analytical Method |
|---|---|---|
| Total Amino Acid | | Automatic Analysis of Amino Acids (except that cystine was oxidized with formic peracid followed by hydrolyzing with hydrochloric acid and that tryptophan was analyzed by means of high performance liquid chromatography) |
| Arginine | 0.93 | |
| Lysine | 1.91 | |
| Histidine | 0.93 | |
| Phenylalanine | 0.65 | |
| Tyrosine | 0.56 | |
| Leucine | 1.77 | |
| Isoleucine | 0.91 | |
| Methionine | 0.63 | |
| Valine | 1.16 | |
| Alanine | 1.44 | |
| Glycine | 1.00 | |
| Proline | 0.60 | |
| Glutamic acid | 3.44 | |
| Serine | 0.92 | |
| Threonine | 1.03 | |
| Aspartic acid | 2.33 | |
| Tryptophan | 0.09 | |
| Cystine | 0.13 | |
| Total Amount | 20.43 | |

EXAMPLE 1

Preparation of Peptide Y-2

26.2 liters of deionized water was added to 800 ml of the sardine peptide α-1000 (liquid) (Brix 45, having a protein content of 29.6%), and passed through a column (1.5×5 cm) filled with an ODS resin (YMC ODS-AQ120-S50) in which peptides contained therein were adsorbed onto the resin. Then, the column was washed with deionized water, and eluted with aqueous, 0%, 10%, 25%, 50% and 99.5% ethanol solutions of 27 liters each in that order to obtain fractions of Y-1, Y-2, Y-3, Y-4 and Y-5, respectively. Of those, Y-2 fraction was concentrated at 40° C. to remove ethanol therefrom, and then freeze-dried to obtain a purified, sardine peptide (Y-2). The Y-2 fraction contained 0.15% of Val-Tyr.

The physicochemical properties of the novel peptide Y-2 of the invention are shown in the following Table 6, Table 7 and Table 8.

TABLE 6

Physicochemical Properties of Y-2 Fraction (1)

Figure 3:
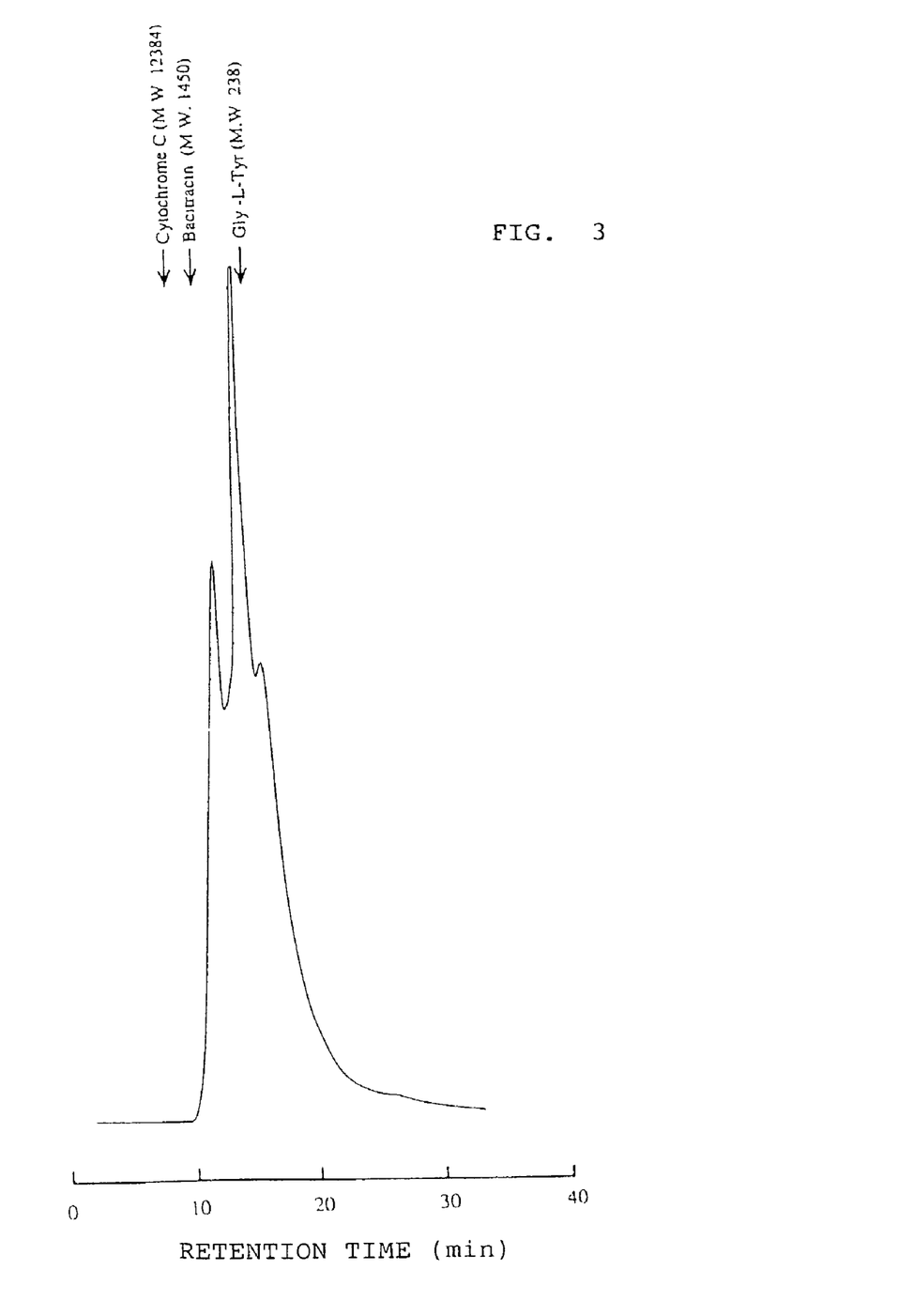
FIG. 3 is a pattern of the molecular weight distribution of peptide Y-2 in gel filtration.

(1) Molecular weight:
200 to 10,000 (measured by Asahipak GS-320 column chromatography) (FIG. 3).

(2) Melting point:
Colored at 138° C. (decomposition point). (Measured in a melting point measuring method according to the general test methods as stated in The Japanese Standards for Food Additives, 5th Ed.)

(3) Specific rotatory power:
$[\alpha]_D^{20} = -51°$ (measured according to a specific rotatory power measuring method according to the general test methods as stated in The Japanese Standards for Food Additives, 5th Ed.)

(4) Solubility in solvents:
Easily soluble in water; but almost insoluble in ethanol, acetone and hexane. (Measured according to the general rules as stated in the 12th Revised Japanese Pharmacopoeia.)

(5) Chemical differentiation in acidic, neutral or basic character:
Neutral, pH of from 5.0 to 8.0 (10% solution).

(6) Appearance:
White or pale yellow powder.

(7) Constituent components:
This contains 5.4% of water (in normal-pressure, heat drying method), 95.3% of protein (in Kjeldahl method with a nitrogen/protein conversion coefficient of 6.25), 0% of lipid (in Soxhlet extraction method), and 1.1% of ash (in direct ashing method).

TABLE 7

Physicochemical Properties of Y-2 Fraction (2)

Figure 4:
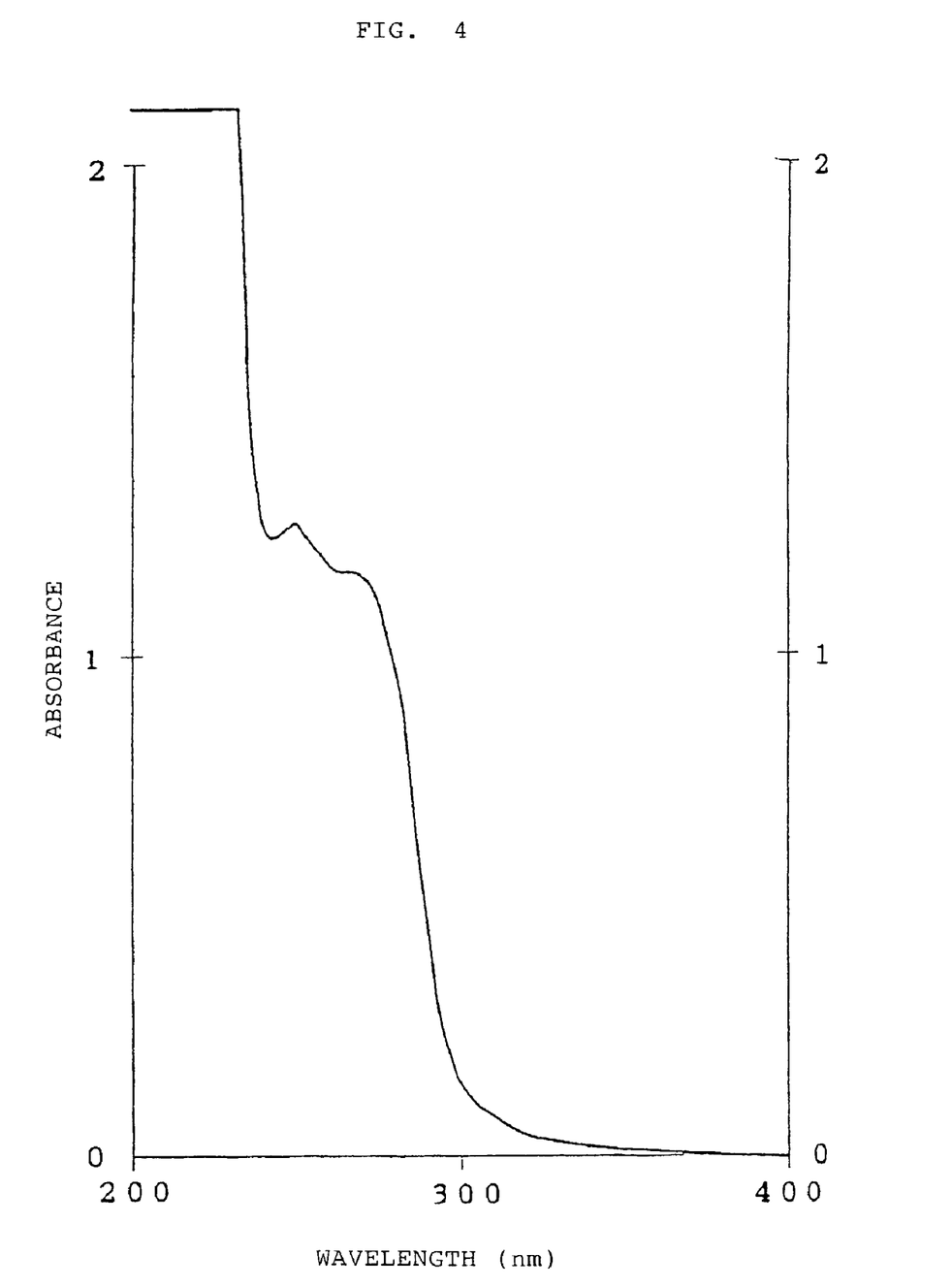
FIG. 4 is a pattern of the UV spectrum of peptide Y-2.

(8) UV spectrum:
(As shown in FIG. 4; measured in an absorbance measuring method according to the general test methods as stated in Japan's Specifications and Standards for Food Additives, 5th Ed.)
Sample: aqueous 0.1% solution.
Device used: UV-240 manufactured by Shimadzu Seisakusho Co.

Figure 5:
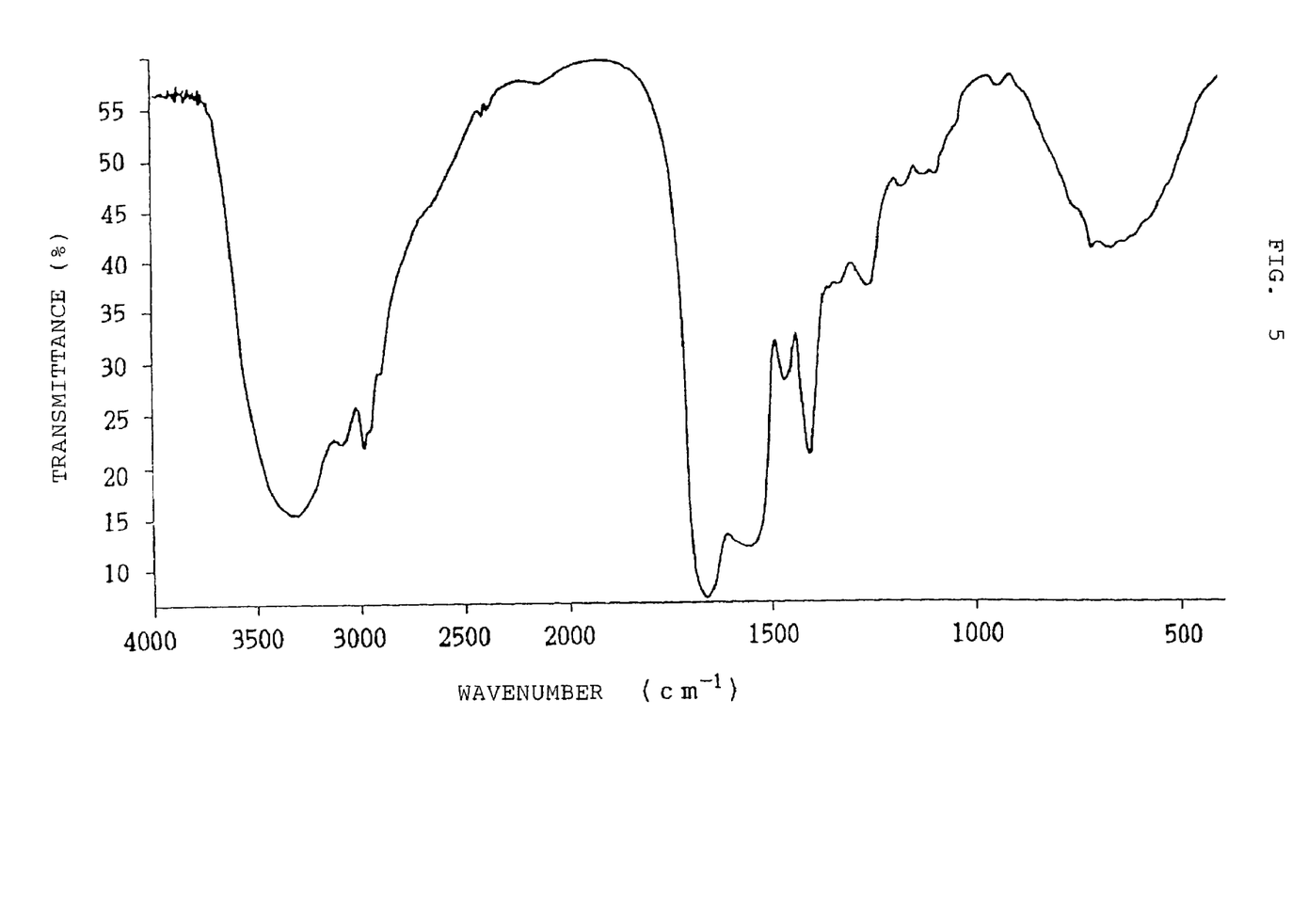
FIG. 5 is a pattern of the IR spectrum of peptide Y-2.

(9) IR spectrum:
(As shown in FIG. 5; measured in a KBr tablet method).
Preparation of sample: mixed with potassium bromide and formed into tablets.
Condition for measurement:
Device used: FT-IR Magna 560 manufactured by Nikole Co.
Resolution: 8 cm.
Integration: 32 times.

(10) Amino acid composition:
As shown in Table 9.
Device used: LC-6A system manufactured by Shimadzu Seisakusho Co.
Detection: OPA method

TABLE 8

Amino Acid Composition of Y-2 Fraction

| Amino Acids | Analytical Data (%) | Analytical Method |
|---|---|---|
| Aspartic acid | 10.97 | Automatic analytical method for amino acids (LC-6A system of Shimadzu) |
| Threonine | 4.10 | |
| Serine | 2.90 | |
| Glutamic acid | 12.52 | |
| Glycine | 4.91 | |
| Alanine | 5.06 | |
| Valine | 6.20 | |
| Methionine | 2.55 | |
| Isoleucine | 5.55 | |
| Leucine | 9.47 | |
| Tyrosine | 2.96 | |
| Phenylalanine | 4.75 | |
| Histidine | 2.83 | |
| Lysine | 10.07 | |
| Arginine | 7.50 | |

EXAMPLE 2

Clinical Examination by Administration of Peptide Y-2

In order to verify the function of peptide Y-2 in human cases, peptide Y-2 in a form of drink was administered to volunteers having high blood pressure whereby the blood pressure depressing effect of the peptide in the tested volunteers was confirmed by means of a continuous administration of peptide Y-2 to them.

A: Preparation of Test Drinks

In administration of the peptide, beverage in a form of drinks were used taking the actual functional food into consideration. One bottle contained 100 ml of the drink, which is easy for continuous administration to human beings. In order to eliminate the difference in the taste between true drink containing the peptide and placebo drink not containing it, both drinks were processed with the necessary but minimum seasonings. Thus, the drinks contained 9.0% of liquid fructose-glucose (High-Craft M-75 manufactured by Nippon Corn Starch), 7.0% of pure honey (manufactured by Fujii Yohosho), 0.12% of stevia extract (High Stevia 100 manufactured by Ikeda Toka Kogyo), 0.2% of sour, and 0.12% of flavoring while, only to the true drink, added was 2.0% of purified, powdery sardine peptide. Accordingly, the true drink contained the purified, sardine peptide Y-2 fraction powder in an amount of 2.0 g/100 ml, and the Val-Tyr content of one true drink was 3 mg/100 ml. To the placebo drink, the purified sardine peptide Y-2 fraction was not added but was replaced with water in them.

All drinks were produced in an actual, integrated production line. Thus, the constituent components weighing 200 kg/batch were formulated, mixed and dissolved at 60° C., then subjected to plate sterilization at 128° C. for 10 seconds, and automatically filled at 90° C. into brown 100 ml bottles having been previously well washed. The bottles thus filled with the drink were left cooled at room temperature and then rapidly cooled with running water in a tank. Labels with the same design were stuck to all the true drink bottles and the placebo drink bottles so that no one of the volunteers, and even the doctors and the nurses in charge of the present clinical examination could differentiate the bottles.

B: Subjects (1) Approval by the Human Investigation Review Committee:

Prior to the present study, the clinical examination was approved by "the Human Investigation Review Committee of the Institute of Health Science, Kyushu University".

(2) Screening of Subjects:

All volunteers were previously informed of the object and the meaning of the present test, the test method, and the safety in the test, and well understood the details of the test. Then, they gave their consent to the test and signed a written certificate for the informed consent. The doctors in charge of the clinical examination checked them by interview, and further checked the data of their medical examinations including electrocardiographs, X-ray photographs of the chest, etc. Based on the medical data of the volunteers thus checked and on their data of previous periodical medical examinations, doctors picked out 46 subjects suitable to the test. The 46 subjects selected as such were subjected to the present clinical examination. They were classified into two groups, on the basis of the standard as stipulated by The US Joint National Committee. Subjects who had a diastolic blood pressure of lower than 85 mmHg and a systolic blood pressure of lower than 130 mmHg in the sitting posture in rest were in one group of normotension (NT group); while subjects with hypertension and subjects with high-normal blood pressure, who both have a diastolic blood pressure of not lower than 85 mmHg and/or systolic blood pressure of not lower than 130 mmHg, were in the other group of hypertension (HT group). Concretely, 12 subjects were in the NT group; and 34 subjects were in the HT group. The subjects in each of those two groups were further classified into a true group for peptide administration and a placebo group for no peptide administration through random sampling. The characteristics of the subjects in each group are shown in the following Table 9.

TABLE 9

|  | Age | SBP | DBP | Height | Weight | BMI |
|---|---|---|---|---|---|---|
| (Group A) |  |  |  |  |  |  |
| average (n = 17) | 44.5 | 146.4 | 90.5 | 166.1 | 65.8 | 23.79 |
| S.E. | ±3.3 | ±2.3 | ±1.8 | ±1.9 | ±2.2 | ±0.6 |
| (Group B) |  |  |  |  |  |  |
| average (n = 17) | 48.8 | 145.3 | 92.1 | 165.6 | 64.7 | 23.51 |
| S.E. | ±3.1 | ±2.6 | ±2.0 | ±2.7 | ±3.3 | ±0.9 |
| F | 0.19 | 0.34 | 0.26 | 0.31 | 0.21 | 0.22 |
| t | 0.91 | 0.25 | 0.64 | 0.17 | 0.29 | 0.29 |
| (Group C) |  |  |  |  |  |  |
| average (n = 17) | 28.3 | 116.8 | 69.3 | 172.7 | 71.9 | 24.01 |
| S.E. | ±2.9 | ±3.2 | ±2.6 | ±2.6 | ±5.8 | ±1.8 |
| (Group D) |  |  |  |  |  |  |
| average (n = 5) | 34.4 | 117.8 | 71.9 | 169.6 | 66.2 | 22.99 |
| S.E. | ±4.1 | ±1.5 | ±1.8 | ±2.9 | ±2.6 | ±0.6 |
| F | 0.33 | 0.04 | 0.16 | 0.48 | 0.04 | 0.02 |
| t | 1.25 | 0.24 | 0.75 | 0.78 | 0.78 | 0.47 |

As shown in the above table, the subjects as classified into the HT group and the NT group depending on their blood pressure were further classified into the true group for peptide administration and the placebo group for no peptide administration. Accordingly, they were classified into four groups A to D which are as follows:

Group A:

Those with SBP≧130 mmHg and/or DBP≧85 mm Hg, to which were administered the true drink twice a day, continuously for 4 weeks.

Group B:

Those with SBP≧130 mmHg and/or DBP≧85 mm Hg, to which were administered the placebo drink twice a day, continuously for 4 weeks.

Group C:

Those with SBP<130 mmHg and/or DBP<85 mm Hg, to which were administered the true drink twice a day, continuously for 4 weeks.

Group D:

Those with SBP<130 mmHg and/or DBP<85 mm Hg, to which were administered the placebo drink twice a day, continuously for 4 weeks.

The meanings of the abbreviations are as follows:
SBP: systolic blood pressure (mmHg).
DBP: diastolic blood pressure (mmHg).
BMI: body mass index.
F: F-test.
t: t-test.

C: Protocol (1) Dosage 4 g of the peptide (Y-2 fraction) was a one-day dosage to a standard male adult who has a body weight of 60 kg (the Val-Tyr content of the Y-2 fraction was considered as 0.15%). In the subacute toxicity test in rats, was confirmed its safety in continuous administration of 2.5 mg/kg·day, in terms of Val-Tyr existing therein, to rats for one month.

(2) Administration Method

For continuous administration, herein made was a randomised double-blind placebo-controlled study in which the subjects were observed as such for two weeks, then the placebo drink was administered to them for one week, then the true drink was administered to them for 4 weeks, and finally the subjects were again observed for 4 weeks. In the true drink administration period, the subjects took one true drink twice a day, in the morning after the breakfast and in the evening before the supper. The subjects were checked for the blood pressure (in the sitting posture) and the pulse once a week, at a predetermined time between 9:30 a.m. and 11:30 a.m. Before and after the drink administration, the body weight of each subject was measured and the blood and the urine of each subject were analyzed.

The time for drink administration, that for blood pressure measurement and that for medical examinations were all strictly defined, but for the others including their meals and behaviors, all subjects were left free.

(3) Test Items and Test Methods

The doctors checked the subjects for the presence or absence of any subjective symptoms and for the objective signs on them by interview and medical diagnosis, and recorded their data. During the test period, the nurses carried out the data measurement and the blood collection. The general physiological test included measurement of the blood pressure, the pulse and the body weight. In measuring the blood pressure and the pulse, the subjects were kept seated in rest at least for 5 minutes before the measurement. Using a continuous automatic blood pressure meter, BP-203RV2 manufactured by Nippon Colin Co., the blood pressure and the pulse were measured continuously three times at intervals of about 2 minutes, and the data were averaged. The averages were recorded as the blood pressure and the pulse of each subject. Throughout the test period, the measurement was effected all the time in the same posture. The medical tests were made before and after the drink administration.

D: Statistical Analysis

The data were represented in terms of the average value±standard error (SE). The time-dependent variations in the medical tests were analyzed in the corresponding t-test. For the blood pressure changes during the period of from 0 to 4 weeks in the continuous administration tests, the data were subjected to variance analysis to determine the significant difference. The level of significance was at most 5%, and the symbols for the test data were as follows:

*: $p<0.001$, : $p<0.01$, *: $p<0.05$.

The test results were analyzed and evaluated as follows. Thus, the data of each group were subjected to (1) a paired t-test before and after the administration and to (2) a group. test for the true group and the placebo group, relative to the average of each group within four weeks for observation period before the administration. For the intervention test, the period for pre-observation before the administration was two weeks, and the data after the administration was subjected to the paired t-test relative to the average in the pre-observation period.

E: Results

1. Subjective Symptoms

During the test period of 12 weeks, all subjects in both the NT group and the HT group showed no subjective symptoms.

2. Blood Pressure and Pulse

Figure 6:
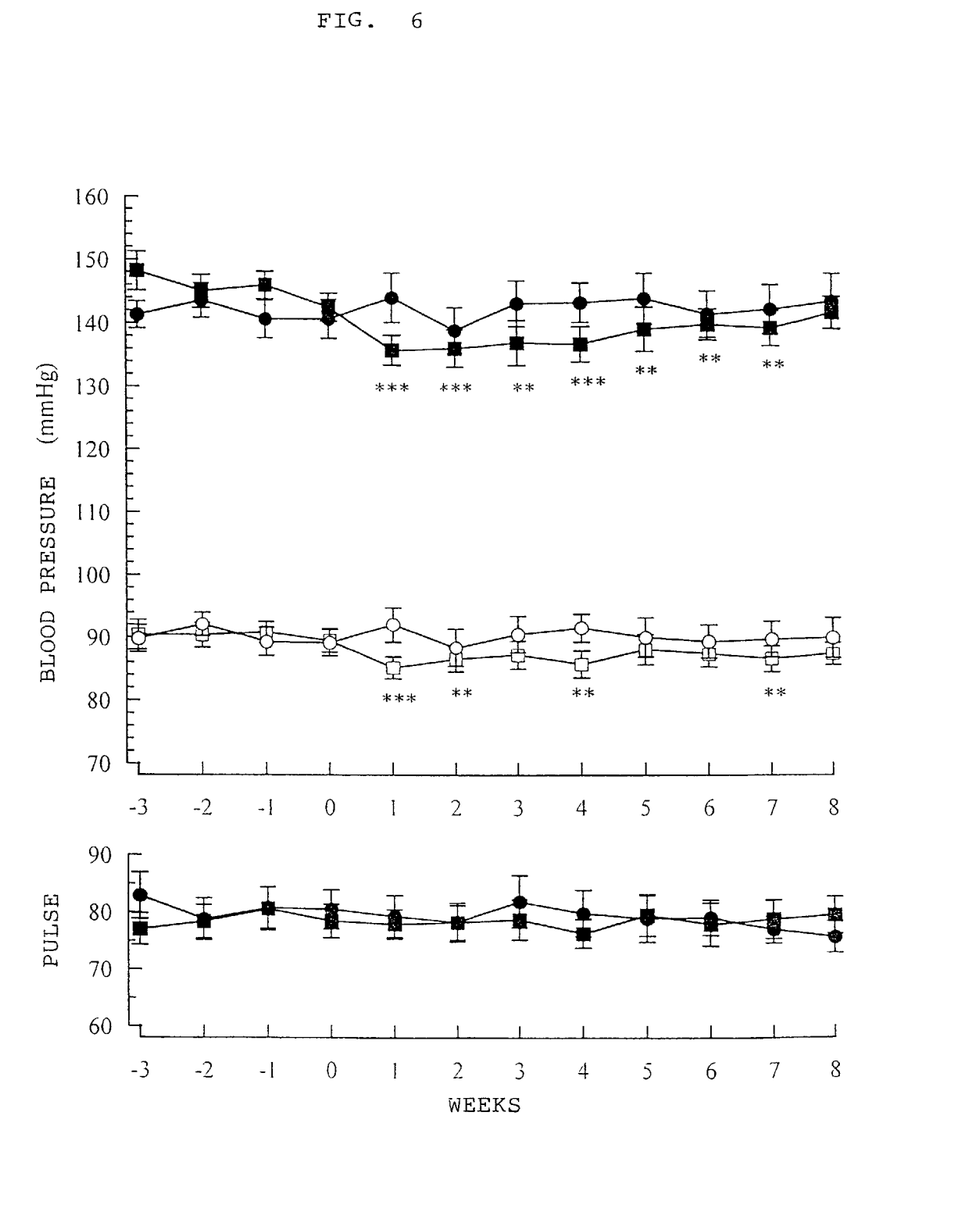
FIG. 6 is a graph showing the data of the blood pressure and the pulse of subjects in an HT group.
Figure 7:
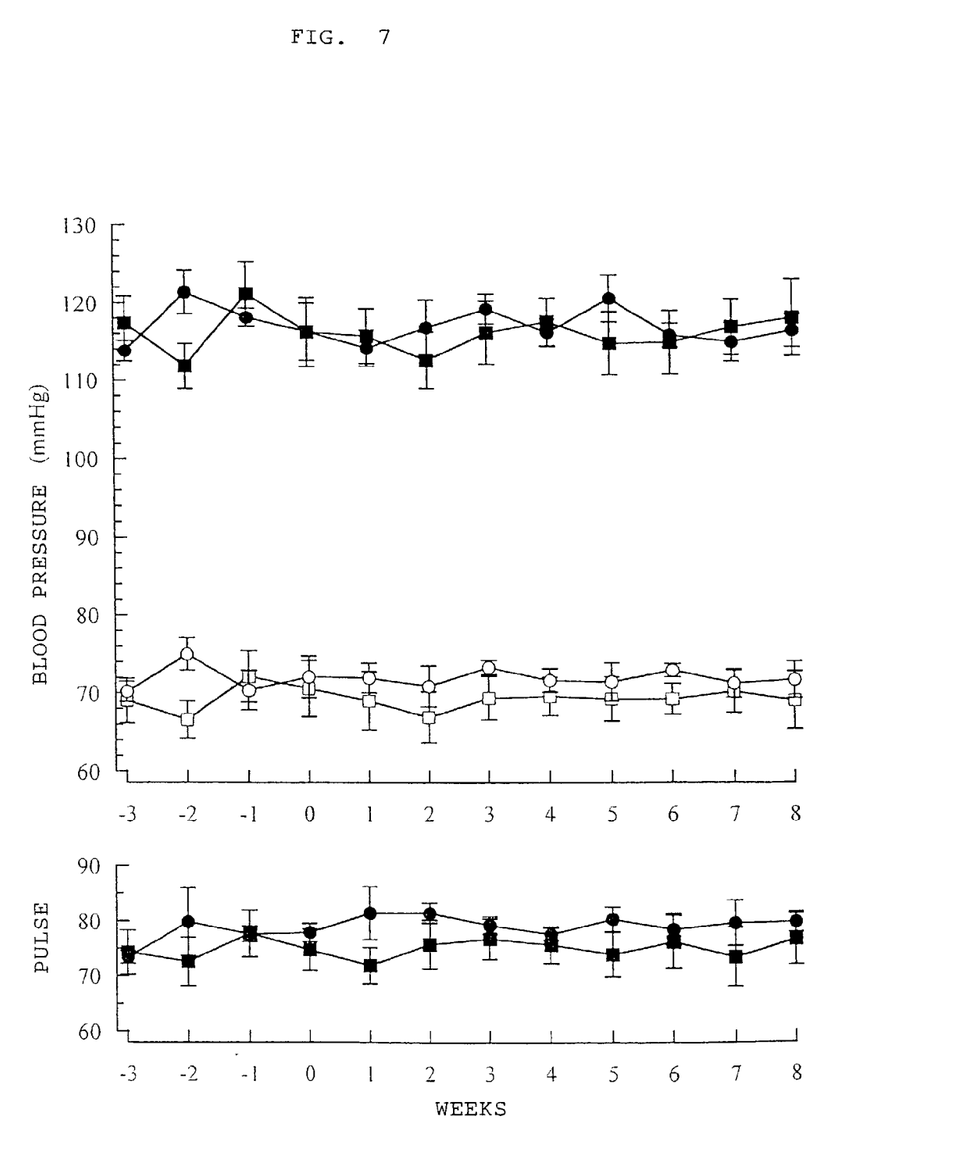
FIG. 7 is a graph showing the data of the blood pressure and the pulse of subjects in an HT group.

The NT group and the HT group each were further classified into the true group for peptide administration and the placebo group for no peptide administration, and the subjects in all these groups were checked for blood pressure and pulse within the test period of 4 weeks and within the post-test period of 4 weeks after the administration test. FIG. 6 and FIG. 7 show the changes in the blood pressure and the pulse of the tested subjects.

FIG. 6 shows the data of the blood pressure and the pulse of the subjects in the hypertension group (HT group), in which ■ and □ indicate the data of SBP and DBP, respectively, of the subjects in the Y-2 administered group (group A), and ● and ○ indicate the data of SBP and DBP, respectively, of the subjects in the placebo group (group B). FIG. 7 shows the data of the blood pressure and the pulse of the subjects in the normotension group (NT group), in which ■ and □ indicate the data of SBP and DBP, respectively, of the subjects in the Y-2 administered group (group C), and ● and ○ indicate the data of SBP and DBP, respectively, of the subjects in the placebo group (group D).

The test results as above verify the following:

1) Normotension Group (NT group)

To 12 subjects in the NT group, who had a systolic blood pressure (SBP) of lower than 130 mmHg and a diastolic blood pressure (DBP) of lower than 85 mmHg, continuously administered was purified sardine peptide (Y-2 fraction) at a dosage of 4 g/day (this corresponds to an amount of Val-Tyr administration of 6 mg/day). As a result, no change for significant difference was admitted in both the blood pressure and the pulse in the paired t-test before and after the peptide administration and in the group test of the true group (group C of 7 subjects) and the placebo group (group D of 5 subjects)(FIG. 7).

2) Hypertension Group (HT group)

Of 34 subjects in the HT group, who had a systolic blood pressure of not lower than 130 mmHg and/or a diastolic blood pressure of not lower than 85 mmHg, 5 subjects in the placebo group stopped the test under unavoidable circumstances as they said during the observation period that they wanted not to participate in the test. After all, 29 subjects in the HT group participated in the test. To them, the same purified sardine peptide (Y-2 fraction, containing Val-Try) as above was administered. As a result, in the paired t-test for the subjects during the administration period (4 weeks) relative to those during the observation period (4 weeks), no change for significant difference was admitted in the blood pressure of the subjects in the placebo group (group B of 12 subjects), but significant blood pressure depression was admitted in the true group (group A of 17 subjects) (FIG. 6).

Thus, in the true group (group A), the maximum blood pressure depression of 9.7 mmHg in SBP and that of 5.2 mmHg in DBP were admitted in one week after the start of the peptide administration. These data were statistically significant at a significance level of 0.1%. The blood pressure depression lasted during the peptide administration period at a significance level of at most 1%, and even in the post-observation period after the administration, the SBP depression significantly lasted within 3 weeks ($p<0.01$) and the DBP depression significantly lasted within 8 weeks ($p<0.05$). After those periods, the blood pressure of the subjects was restored to the original condition as in the initial observation period.

In the group test of the true group (group A) and the placebo group (group B), the subjects in the true group had significant blood pressure depression relative to those in the placebo group. Concretely, the maximum SBP depression was 12.1 mmHg and the maximum DBP depression was 7.1 mmHg in one week after the start of the peptide administration. Also in this group, the blood pressure depression significantly lasted within 3 weeks in the post-observation period that followed the administration period. After those periods, the blood pressure of the subjects was restored to the original condition as in the pre-observation period.

During the test, all subjects in all groups had no abnormality in the pulse.

3. Clinical Examination Results

Before and after the administration test, the subjects were subjected to a peripheral blood and biochemical blood examination and to a 24-hour urinary test, and their varying data were recorded. Any group had significant differences in evaluations of hematocrit value (Ht) and erythrocyte-related values (MCV, MCH, MCHC) in statistics in the peripheral blood examination, but all of the data variations were negligible in clinical aspects, as being within the normal variation ranges.

EXAMPLE 3

Figure 8:
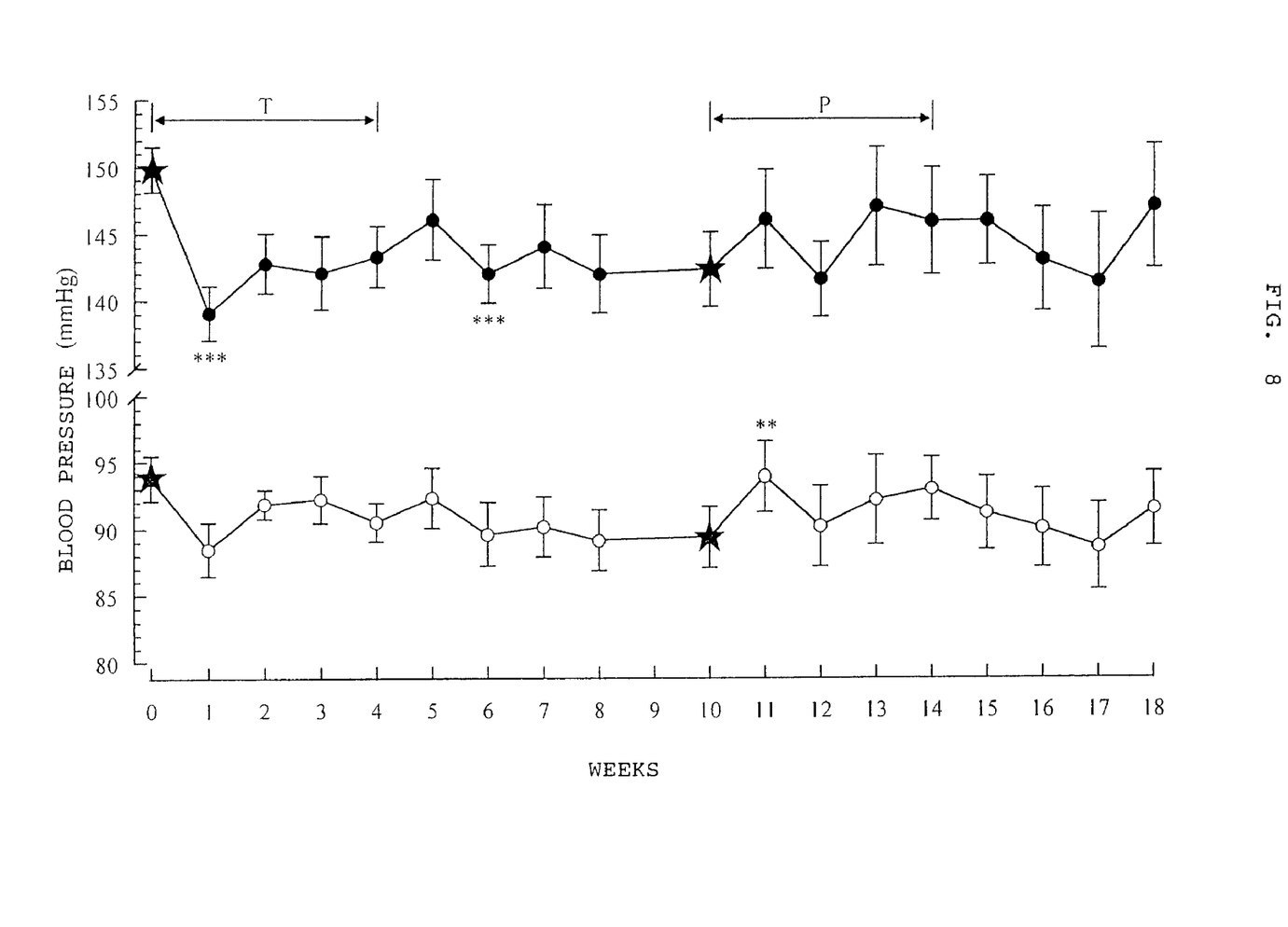
FIG. 8 is a graph showing the data in an intervention test.

Intervention Test 7 subjects in the true group of the HT group were subjected to an intervention test, in which they took the placebo drink after the control observation period of 2 weeks that followed the post-administration period of 4 weeks after the true administration period (FIG. 8). As a result, in the true administration period, they had a maximum blood pressure depression (of 10.8 mmHg for SBP and 5.3 mmHg for DBP) in one week, as in the previously described test, and the significant blood pressure depression in them lasted for 4 weeks. After the period, the blood pressure inclined gradually toward the original condition. The placebo drink was administered to them after the wash-out period of 6 weeks. During the placebo administration period, the blood pressure of the subjects did not decrease relative to that in the post-observation period, but rather increased for restoration. During this period, the blood pressure restoration was gentle. The data verify the long-lasting blood pressure-depressing effect of the peptide of the invention.

In the drawing, ● and ○ indicate the SBP value and the DBP value of the tested subjects; the asterisks indicate the average blood pressure; P indicates the placebo drink; and T indicates the true drink. Regarding the level of significance, the symbols for the test data are as follows: : $p<0.01$, *: $p<0.001$.

EXAMPLE 4

Peptide Y-2 exhibited satisfactory blood pressure depressing effect at a dosage of 4 g/day (this corresponds to an amount of Val-Tyr of 6 mg/day). For its practical use in functional foods, the economical aspect will be a significant factor. The present study is to confirm the minimum peptide dosage for effective blood pressure depression, in which the peptide dosages were stepwise varied to find the limit value for the effectiveness of the peptide.

A: Protocol

Under the same conditions as mentioned previously, subjects were tested for the minimum effective dosage of peptide Y-2 thereto. The basic composition of the test drinks and the grouping of the subjects were the same as previously.

(1) Subjects

The present study was to confirm the minimum effective dosage of peptide Y-2 for blood pressure depression. Therefore, only the subjects having a higher blood pressure than normal high blood pressure in the HT group were sampled at random and tested herein. They were classified into a true group of 14 subjects (average age of 45.1±3.5, having a systolic blood pressure of 144.5±2.7 mmHg and a diastolic blood pressure of 90.7±1.8 mmHg both on average), and a placebo group of 5 subjects (average age of 50.4±4.9, having a systolic blood pressure of 147.3±2.9 mmHg and a diastolic blood pressure of 92.0±2.8 mmHg both on average).

(2) Dosage

In the previous in vivo tests, peptide Y-2 was proved effective at a dosage of from 10 to 100 μg/kg in terms of Val-Tyr in the peptide. However, in consideration of the difference between rats and human beings and the difference between intravenous injection and oral administration, the lowermost dosage in the present study was below 10 μg/kg, and the dosage was gradually increased to find the marginal dose indispensable for the efficacy expression of the peptide. Concretely, the dosage of the purified sardine peptide (Y-2 fraction) was stepwise increased two-fold from 0.25 g/day (6.25 μg/kg·day, in terms of the Val-Tyr content of the peptide), to 0.50 g/day (12.5 μg/kg·day, in terms of the Val-Tyr content of the peptide), and to 1.00 g/day (25 μg/kg·day, in terms of the Val-Tyr content of the peptide).

Administration Method

After an observation period of 2 weeks, the true drink was administered to the subjects at a predetermined dosage for 2 weeks, and the dosage was varied at intervals of 2 weeks. As in the previously described tests, the subjects took the respective drinks twice a day, in the morning and in the evening, and the test was ceased after the period when the effectiveness of the peptide for blood pressure depressing was confirmed.

B. Results

Figure 9:
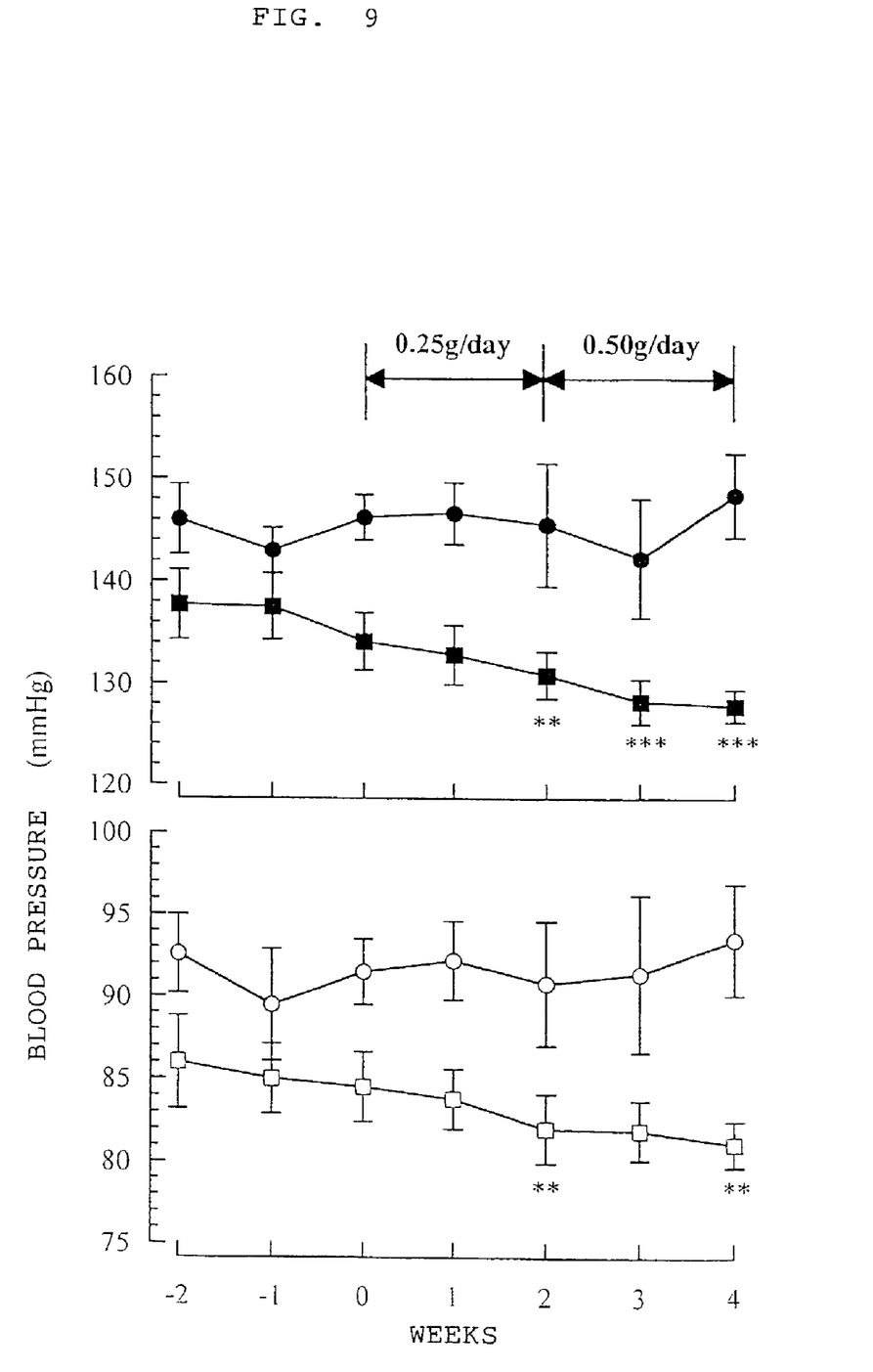
FIG. 9 is a graph showing the blood pressure change relative to the dose change.

The data obtained are shown in FIG. 9. FIG. 9 shows the blood pressure change in the subjects of the hypertension group (HT group), depending on the change in dosage of peptide Y-2 (sardine peptide) thereto, in which ■ and □ indicate the SBP value and the DBP value, respectively, of the Y-2 administered subjects of the true group, and ● and ○ indicate the SBP value and the DBP value, respectively, of the placebo administered subjects of the placebo group.

As shown in FIG. 9, the purified sardine peptide (Y-2 fraction) was administered to the subjects of the true group at an initial dosage of 0.25 g/day. In two weeks, the systolic blood pressure of the subjects decreased by 5.6 mmHg as compared with the initial value and the diastolic blood pressure thereof decreased by 3.2 mmHg as compared with the same. In both SBP and DBP, the significant difference was admitted in statistics, for which the level of significance was 5%. After the initial stage of third week, the dosage was increased to 0.50 g/day whereupon, in the third week, the systolic blood pressure of the subjects decreased by 8.2 mmHg as compared with the initial value and the diastolic blood pressure thereof decreased by 3.3 mmHg as compared with the same. In SBP, the significant difference was admitted in statistics, for which the level of significance was 1%. Regarding the level of significance, the symbols for the test data are as follows: **: $p<0.01$, *: $p<0.05$.

On the other hand, in the placebo group, little change in the blood pressure was found. There was found no abnormality in the pulse of the subjects of the two groups. From the data as above, it is understood that the peptide of the invention is effective for blood pressure depression in human beings at a dosage of 0.25 g/day (6.25 μg/kg·day, in terms of the Val-Tyr content of the peptide) in statistics, and the level of significance at the effective dosage of 0.50 g/day (12.5 μg/kg·day, in terms of the Val-Tyr content of the peptide) is 1%. Even at the dose of 0.25 g/day (6.25 μg/kg·day, in terms of the Val-Tyr content of the peptide), the blood pressure of the subjects gradually decreased immediately after the start of the peptide administration. Therefore, it is understood that the peptide of the invention will be practically well effective for blood pressure depression in human beings even at that minimum dosage of 0.25 g/day so far as the peptide administration is continued for a long period of time. When the practical minimum effective dosage of the peptide is regarded as 0.25 g/day (6.25 μg/kg·day, in terms of the Val-Tyr content of peptide), there was found no problematic changes in blood biochemical aspects and in other clinical aspects, even in the peptide administration as in the previously-described test for 28 days at a dosage of 16 times said minimum effective dosage. In addition, the subjects' reply to the doctor's question did not show any side effects as in the case of commercially-available ACE inhibitors.

EXAMPLE 5

Preparation of Drink

| (Formulation) | |
|---|---|
| Liquid fructose-glucose | 9.0% |
| Pure honey | 7.0% |
| Stevia extract | 0.12% |
| Sour (citric acid) | 0.2% |
| Flavoring | 0.12% |
| Peptide Y-2 | 0.125% |
| Pure water added to make | 100% in total |

The constituent components as above were mixed and dissolved at 60° C., and subjected to plate sterilization at 128° C. for 10 seconds. This was filled into a brown 100-ml bottle having been well washed, at 90° C., left cooled at room temperature, and then rapidly cooled with running water in a tank whereupon a drink was produced.

The resulting drink was subjected to analytical test and amino acid composition measurement and the results obtained are shown in Table 10 and Table 11, respectively.

TABLE 10

Result of Analytical Test

| Items for Analytical Test | Result | Comment | Analytical Method |
|---|---|---|---|
| Water | 86.9 g/100 g | | Vacuum heating drying method |
| Protein | 0.3 g/100 g | 1 | Kjeldahl method |
| Lipid | 0 g/100 g | | Soxhlet method |
| Fiber | 0 g/100 g | | Improved Henneberg Stohman method |
| Ash | 0 g/100 g | | Direct ashing method |
| Saccharide | 12.8 g/100 g | 2 | |
| Energy | 52 kcal/100 g | 3 | |
| Sodium | 1.1 mg/100 g | | Atomic absorption spectrometry |

Note 1: Nitrogen protein conversion coefficient: 6.25
Note 2: Calculating formula: 100 − (water + protein + lipid + fiber + ash)
Note 3: Energy conversion coefficient: protein, 4; lipid, 9; carbohydrate (fiber + saccharide), 4

TABLE 11

Amino Acid Composition (mg/100 g sample)

| | Total amino acid amount |
|---|---|
| Aspartic acid | 23.2 |
| Threonine | 8.6 |
| Serine | 6.9 |
| Glutamic acid | 30.0 |
| Proline | 18.0 |
| Glycine | 18.4 |
| Alanine | 11.7 |
| Cystine | — |
| Valine | 14.7 |
| Methionine | 6.3 |
| Isoleucine | 13.1 |
| Leucine | 19.7 |
| Tyrosine | 3.6 |
| Phenylalanine | 11.6 |
| Histidine | 6.7 |
| Lysine | 19.1 |
| Arginine | 17.1 |
| Total | 228.7 mg |

Note:
— = not detected

ADVANTAGE OF THE INVENTION

In accordance with the present invention, the following significant advantages have been achieved. Thus, on the basis of the finding that ACE-inhibiting peptide which is latently present in sardine protein is made actually present and is made in high concentrations whereby the said peptide can be prepared into a functional food material having excellent taste and stability in vivo and showing high safety, actual functional drink has been prepared and its clinical test has been carried out to subjects of normal high blood pressure including mild hypertension whereupon the following advantages have been confirmed.

1) Drink (100 ml/bottle) where each bottle contained 2.0 g (3 mg as Val-Tyr) of purified sardine peptide Y-2 fraction which was an ODS-treated 10% ethanolic eluted fraction was prepared. Twelve volunteers having a normal blood pressure (lower than 130 mmHg of systolic blood pressure and lower than 85 mmHg of diastolic blood pressure) were classified into two groups where one group consisted of 7 and another consisted of 5. True drink containing the peptide was administered to the 7 volunteers while placebo drink (a blank) was administered to the 5 volunteers at the dosage of two bottles per day (6 mg/day as a Val-Tyr dosage of a true group) for four weeks and a random double-blind control test was carried out whereupon it was found that there was no significant difference in blood pressure changes and that the present peptide showed no influence at all to blood pressure and pulse of NT group.

2) In the said test, hematic biochemical test and urinary test were carried out by collecting the blood immediately before initiation of administration of the peptide and at 4 weeks after the administration and also by collecting 24-hour urine whereupon, although variations were noted in some items, they were slight ones within a normal data range and were no problematic matter in clinics. There was no abnormality in other clinical tests and subjective symptoms and it was shown that there was no problem at all for the clinical safety of the present peptide to subjects showing normal blood pressure.

3) Volunteers showing a systolic blood pressure of 130 mmHg or higher and/or a diastolic blood pressure of 85 mmHg or higher were classified by random sampling into a true group and a placebo group and a random double-blind control test was carried out for 29 volunteers in total whereupon, in a paired t-test, the systolic blood pressure and the diastolic blood pressure significantly lowered (p<0.001) to an extent of 9.7 mmHg and 5.2 mmHg, respectively, in the first week in a true group. Thus, a hypotensive effect of the present peptide to human being was ascertained.

4) Even when administration period of the peptide was made 4 weeks and, on the fifth week and thereafter, administration was ceased in the above test, hypotension was still noted significantly (p<0.05) during 3 weeks until the seventh week whereupon duration of the hypotensive effect of the present peptide was ascertained.

5) When 7 cases were randomly sampled from the HT group and an intervention test from a true administration to a placebo administration was carried out, a significant blood pressure depression was noted in the case of administration of the true drink while, upon administration of the placebo, no blood pressure depression was noted whereupon the blood pressure depression effect of the present test was supported to be due to the present peptide.

6) On the other hand, in the clinical test result before and after the administration, variations were noted in some items but all of them were slight and within a normal variation range and there was no problem at all in terms of clinics. Onset of subjective symptom was not noted at all as well. Accordingly, safety of the present peptide by a continuous administration was shown.

7) For a practical application of sardine peptide as a functional food, an investigation for its minimum effective dosage was carried out and, at the dosage of 0.75 mg (as Val-Tyr)/day, a significant (p<0.01) lowering effect was noted to an extent of 8.2 mmHg and 3.3 mmHg for a systolic blood pressure and for a diastolic blood pressure, respectively.

8) Throughout the whole test period, there was no side effect such as cough and eruption at all which had been noted in the currently available ACE inhibitors whereby it was ascertained that the present peptide was a quite safe and a highly effective material as a functional food to be taken usually.

In the case of separation and extraction of food materials having a high function from food, its safety is an essential condition and, since the present peptide was noted to have a sufficient hypotensive effect to the persons of mild hyper tension and normal hypertension and was ascertained to show a high safety without side effect such as cough as a result of clinical investigation, the present peptide is now expected to be a quite significant food material toward an aging society in future.

The invention claimed is:

1. A method for reducing blood pressure, which comprises:

administering to a subject in need thereof a pharmaceutical composition comprising a mixture of peptides and a pharmaceutically acceptable carrier so that an effective amount of Valyl-Tyrosine contained in the mixture of peptides is administered, wherein the mixture of peptides has the following properties:

(a) molecular weight: 200 to 10,000 Daltons;

(b) melting point: colored and decomposed at 138° C.;

(c) water soluble;

(d) almost insoluble in ethanol, acetone and hexane; and (e) an infrared spectrum showing absorbance peaks at approximately 3350 $cm^{-1}$, 2980 $cm^{-1}$, 1670 $cm^{-1}$, 1550 $cm^{-1}$, 1460 $cm^{-1}$, 1400 $cm^{-1}$ and 1250 $cm^{-1}$.

2. The method according to claim 1, wherein the mixture of peptides has the following amino acid composition:

| | |
|---|---|
| Aspartic acid | 11% |
| Threonine | 4.1% |
| Serine | 2.9% |
| Glutamic Acid | 13% |
| Glycine | 4.9% |
| Alanine | 5.1% |
| Valine | 6.2% |
| Methionine | 2.6% |
| Isoleucine | 5.6% |
| Leucine | 9.5% |
| Tyrosine | 3.0% |
| Phenylalanine | 4.8% |
| Histidine | 2.8% |
| Lysine | 10% |
| Arginine | 7.5%. |

3. The method according to claim 2, wherein the effective amount of Valyl-Tyrosine is an amount in the range of from 6.25 μg to 100 μg per kilogram body weight per day.

4. The method according to claim 2, in which the effective amount of Valyl-Tyrosine is an amount in the range of from 6.25 μg to 25 μg per kilogram body weight per day.

5. A method for reducing blood pressure, said method comprising:

a subject in need thereof ingesting a food comprising a mixture of peptides and a food ingredient(s) so that an effective amount of Valyl-Tyrosine contained in the mixture of peptides is ingested, wherein the mixture of the peptides has the following properties:

(a) molecular weight: 200 to 10,000 Daltons;

(b) melting point: colored and decomposed at 138° C.;

(c) water soluble;

(d) almost insoluble in ethanol, acetone and hexane; and (e) an infrared spectrum showing absorbance peaks at approximately 3350 $cm^{-1}$, 2980 $cm^{-1}$, 1670 $cm^{-1}$, 1550 $cm^{-1}$, 1460 $cm^{-1}$, 1400 $cm^{-1}$ and 1250 $cm^{-1}$.

6. The method according to claim 5, wherein the mixture of peptides has the following amino acid composition:

| | |
|---|---|
| Aspartic acid | 11% |
| Threonine | 4.1% |
| Serine | 2.9% |
| Glutamic Acid | 13% |
| Glycine | 4.9% |
| Alanine | 5.1% |
| Valine | 6.2% |
| Methionine | 2.6% |
| Isoleucine | 5.6% |
| Leucine | 9.5% |
| Tyrosine | 3.0% |
| Phenylalanine | 4.8% |
| Histidine | 2.8% |
| Lysine | 10% |
| Arginine | 7.5%. |

7. The method according to claim 5, wherein the effective amount of Valyl-Tyrosine is an amount in the range of from 6.25 µg to 100 µg per kilogram body weight per day.

8. The method according to claim 6, wherein the effective amount of Valyl-Tyrosine is an amount in the range of from 6.25 µg to 100 µg per kilogram body weight per day.

\* \* \* \* \*